United States Patent
Tsubota et al.

(10) Patent No.: US 8,164,049 B2
(45) Date of Patent: Apr. 24, 2012

(54) RADIATION DETECTING APPARATUS, RADIATION IMAGE CAPTURING SYSTEM, AND TEMPERATURE COMPENSATING METHOD

(75) Inventors: Keiji Tsubota, Minami-ashigara (JP); Yutaka Yoshida, Fuchu (JP); Eiichi Kito, Minami-ashigara (JP); Yasunori Ohta, Yokohama (JP); Naoyuki Nishino, Minami-ashigara (JP); Shinji Imai, Hadano (JP); Yasuhiro Seto, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 376 days.

(21) Appl. No.: 12/461,536

(22) Filed: Aug. 14, 2009

(65) Prior Publication Data
US 2010/0051795 A1  Mar. 4, 2010

(30) Foreign Application Priority Data

Aug. 28, 2008 (JP) .................................. 2008-219656
Jun. 23, 2009 (JP) .................................. 2009-148744

(51) Int. Cl.
*G01D 18/00* (2006.01)

(52) U.S. Cl. .................................................. 250/252.1
(58) Field of Classification Search ............... 250/252.1, 250/370.08, 370.09; 348/E5.081
See application file for complete search history.

(56) References Cited

U.S. PATENT DOCUMENTS
2006/0169907 A1* 8/2006 Shinden .................. 250/370.09
2007/0183571 A1* 8/2007 Spahn ............................ 378/98

FOREIGN PATENT DOCUMENTS
JP  2002-357664  12/2002
JP  2006-128890  5/2006
JP  2007-229366  9/2007

* cited by examiner

*Primary Examiner* — Mark R Gaworecki
(74) *Attorney, Agent, or Firm* — Jean C. Edwards, Esq.; Edwards Neils PLLC

(57) ABSTRACT

A radiation detecting apparatus includes a radiation conversion panel for detecting the radiation which has passed through the subject and converting the detected radiation into radiation image information, a temperature sensor for detecting a temperature of the radiation conversion panel, and a sensitivity corrector for correcting at least one of a sensitivity, a dark current, a density step, and a residual image of the radiation conversion panel based on the temperature detected by the temperature sensor.

10 Claims, 9 Drawing Sheets

RADIATION DETECTING APPARATUS, RADIATION IMAGE CAPTURING SYSTEM, AND TEMPERATURE COMPENSATING METHOD

CROSS-REFERENCE TO RELATED APPLICATIONS

This application is based upon and claims the benefit of priority from Japanese Patent Application No. 2008-219656 filed on Aug. 28, 2008 and Japanese Patent Application No. 2009-148744 filed on Jun. 23, 2009 in the Japanese Patent Office, of which the contents are incorporated herein by reference.

BACKGROUND OF THE INVENTION

1. Field of the Invention

The present invention relates to a radiation detecting apparatus incorporating a radiation conversion panel for detecting a radiation which has passed through a subject and converting the detected radiation into radiation image information, and a radiation image capturing system incorporating such a radiation detecting apparatus. The present invention is also concerned with a temperature compensating method for compensating a change in the temperature of a radiation conversion panel.

2. Description of the Related Art

In the medical field, there have widely been used radiation image capturing systems which apply a radiation to a subject and guide the radiation that has passed through the subject to a radiation conversion panel, which captures a radiation image from the radiation. Known forms of the radiation conversion panel include a conventional radiation film for recording a radiation image by way of exposure, and a stimulable phosphor panel for storing a radiation energy representing a radiation image in a phosphor and reproducing the radiation image as stimulated light by applying stimulating light to the phosphor. The radiation film with the recorded radiation image is supplied to a developing device to develop the radiation image, or the stimulable phosphor panel is supplied to a reading device to read the radiation image as a visible image.

In the operating room or the like, it is necessary to read recorded radiation image information immediately from a radiation conversion panel after the radiation image information is captured therein for the purpose of quickly and appropriately treating the patient. As a radiation conversion panel which meets such a requirement, there has been developed a direct-conversion-type radiation conversion panel for directly converting a radiation into an electric signal or an indirect-conversion-type radiation conversion panel which comprises a scintillator for temporarily converting a radiation into visible light and solid-state detectors for converting the visible light into an electric signal to read detected radiation image information.

It has been proposed in Japanese Laid-Open Patent Publication No. 2002-357664 to detect, with a load sensor, a load applied to the radiation-irradiated surface of a radiation detecting device which houses a radiation detector (radiation conversion panel) therein, and correct dark-current characteristics and sensitivity characteristics of the radiation conversion panel based on the detected load.

Japanese laid-open patent publication No. 2006-128890 discloses that the temperature status of a radiation conversion panel is grasped by detecting the temperature of the radiation conversion panel with a temperature sensor, and if the detected temperature deviates from a given temperature range, then a warning is issued and the radiation conversion panel is de-energized.

Japanese Laid-Open Patent Publication No. 2007-229366 reveals a radiation image capturing apparatus including an integral amplifier and an A/D converter which are connected to the output terminal of a radiation conversion panel. Offsets and gain fluctuations of the integral amplifier and the A/D converter which are caused by temperature changes thereof are reduced.

For capturing radiation image information of a subject, the subject is held in contact with a radiation detecting apparatus, and a radiation is applied to the subject. While the subject is being irradiated with the radiation, i.e., while the radiation image information of the subject is being captured, the heat of the subject is transferred to a radiation conversion panel housed in the radiation detecting apparatus, increasing the temperature of the radiation conversion panel. Therefore, at least one of a sensitivity, a dark current, a density step, and a residual image of the radiation conversion panel tends to change.

However, Japanese Laid-Open Patent Publication No. 2002-357664, Japanese Laid-Open Patent Publication No. 2006-128890, and Japanese Laid-Open Patent Publication No. 2007-229366 fail to disclose or propose anything about temperature compensation for a change in at least one of the sensitivity, the dark current, the density step, and the residual image of the radiation conversion panel, which is caused by a temperature change of the radiation conversion panel.

SUMMARY OF THE INVENTION

It is an object of the present invention to perform reliable temperature compensation for a change in at least one of a sensitivity, a dark current, a density step, and a residual image of a radiation conversion panel, which is caused by a temperature change of the radiation conversion panel.

According to the present invention, a radiation which has passed through a subject is detected and converted into radiation image information by a radiation conversion panel of a radiation detecting apparatus. A temperature of the radiation conversion panel is detected by a temperature detecting unit, and at least one of a sensitivity, a dark current, a density step, and a residual image of the radiation conversion panel is corrected by a corrector based on the temperature detected by the temperature detecting unit.

Since the corrector corrects at least one of the sensitivity, the dark current, the density step, and the residual image of the radiation conversion panel based on the temperature detected by the temperature detecting unit, it is possible to perform temperature compensation reliably with respect to a change in at least one of the sensitivity, the dark current, the density step, and the residual image which is caused by a change in the temperature of the radiation conversion panel.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
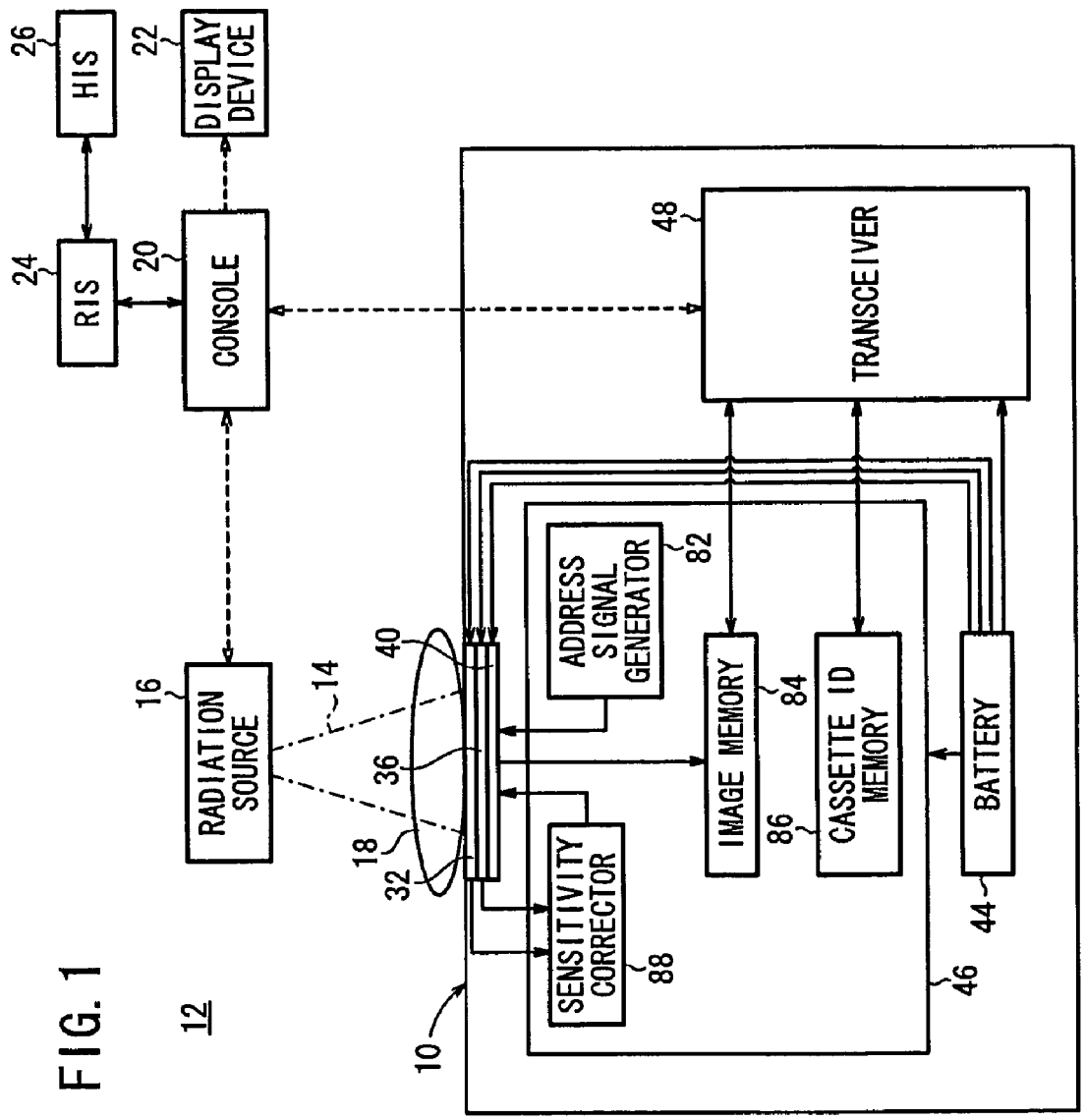
FIG. 1 is a block diagram of a radiation image capturing system according to an embodiment of the present invention.

FIG. 1 shows in block form a radiation image capturing system 12 which incorporates a radiation detecting apparatus (hereinafter also referred to as "radiation detecting cassette") 10 according to an embodiment of the present invention.

The radiation image capturing system 12 comprises a radiation source 16 for applying a radiation 14 at a dosage according to image capturing conditions to a patient 18 as a subject, a radiation detecting cassette 10 housing therein a radiation detector (radiation conversion panel) 40 for detecting the radiation 14 which has passed through the patient 18, a display device 22 for displaying radiation image information based on the radiation 14 detected by the radiation detector 40, and a console (control apparatus) 20 for controlling the radiation detecting cassette 10, the radiation source 16, and the display device 22. Signals are sent and received between the console 20, the radiation detecting cassette 10, the radiation source 16, and the display device 22 based on WiFi (Wireless Fidelity) or millimeter-wave wireless communications according to the UWB (Ultra-Wide Band) technology or IEEE 802.11. a/g/n. The console 20 is connected to a radiology information system (RIS) 24 which generally manages radiation image information handled by the radiological department of the hospital and other information. The RIS 24 is connected to a hospital information system (HIS) 26 which generally manages medical information in the hospital.

Figure 2:
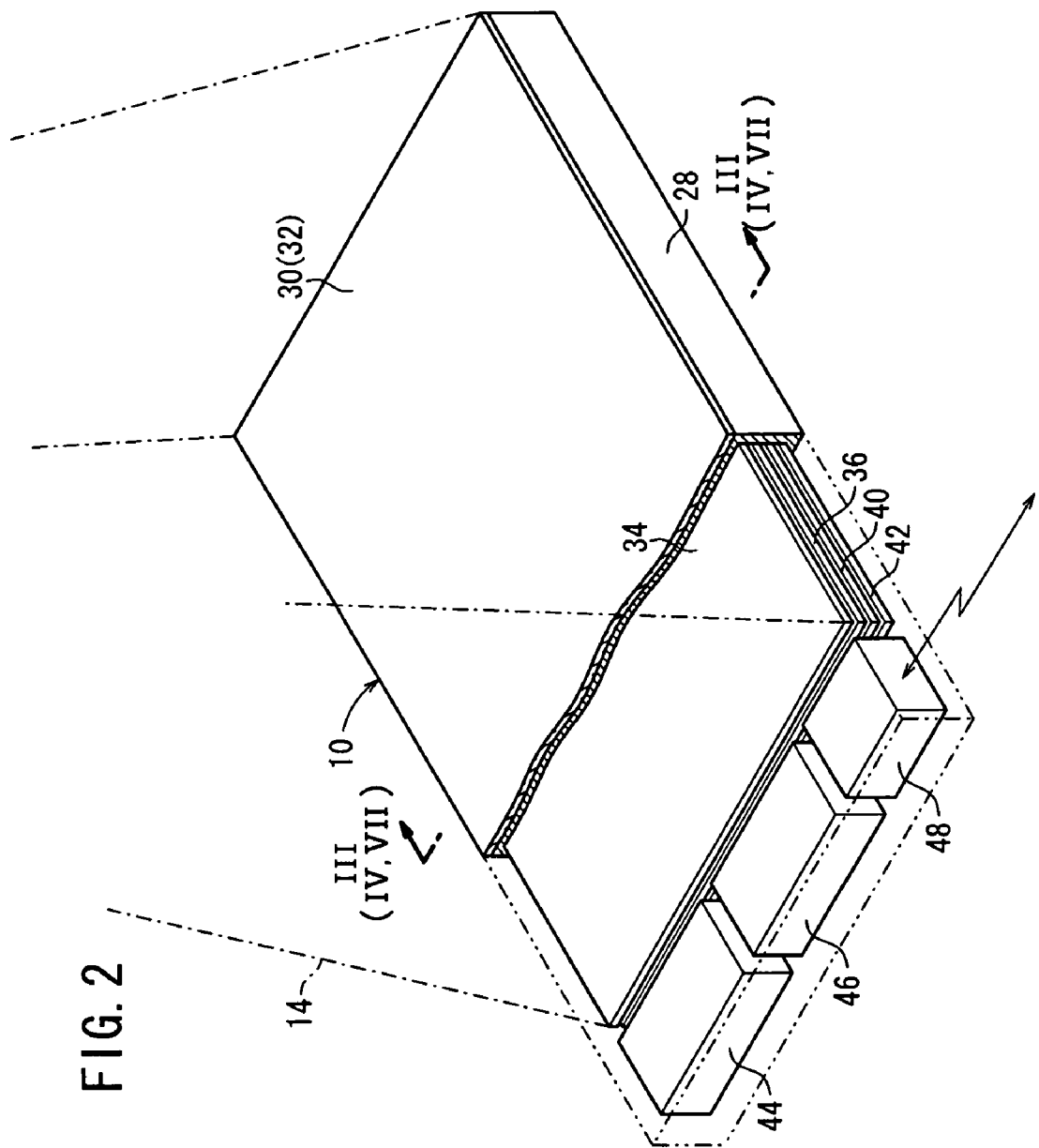
FIG. 2 is a perspective view, partly cut away, showing internal structural details of a radiation detecting cassette in the radiation image capturing system shown in FIG. 1.
Figure 3:
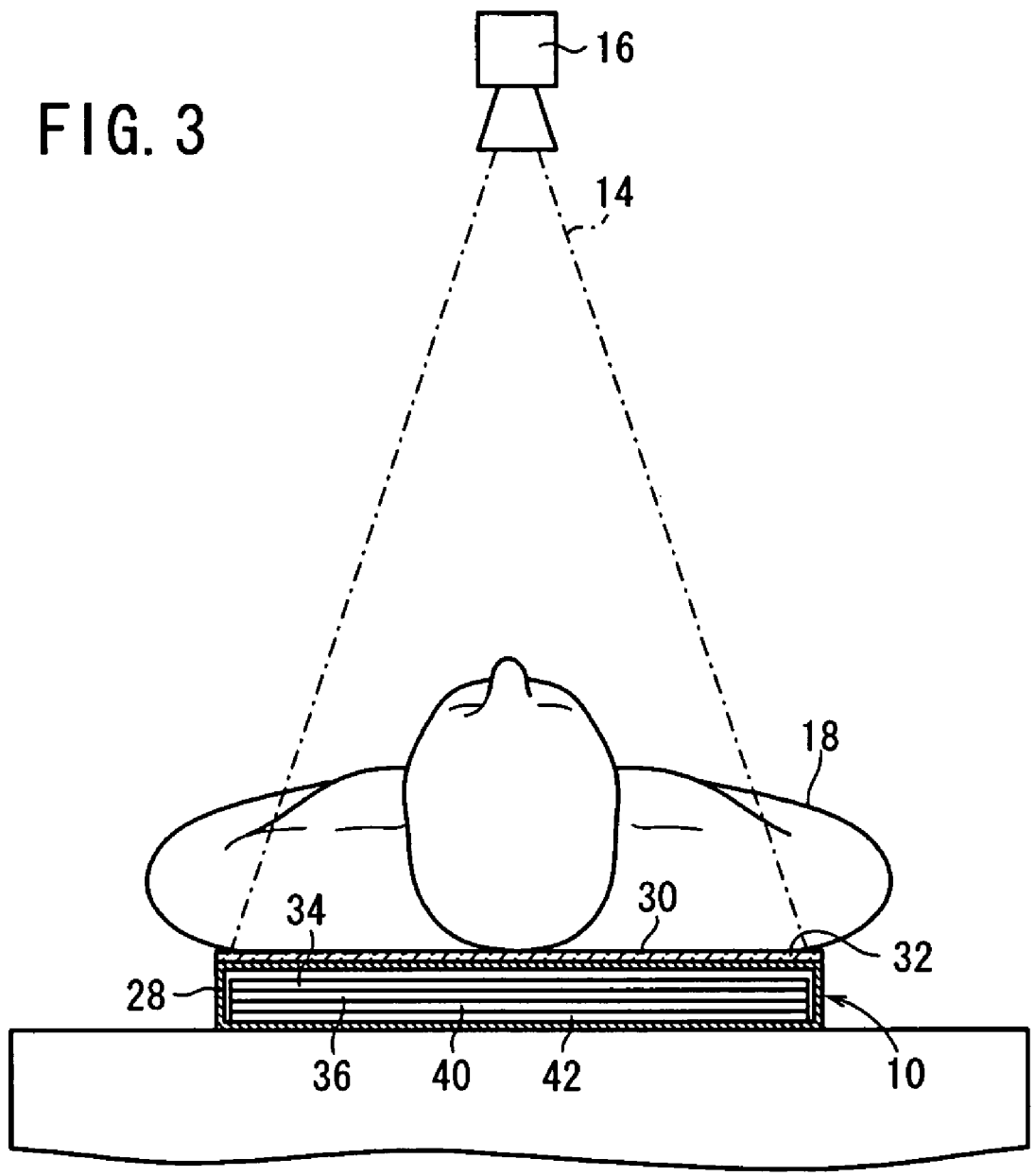
FIG. 3 is an elevational view of a radiation source and a patient, with the radiation detecting cassette being shown in a cross section taken along line III-III of FIG. 2.

As shown in FIGS. 2 and 3, the radiation detecting cassette 10 has a substantially rectangular casing 28 made of a material permeable to the radiation 14. The casing 28 has a surface 30 which is irradiated with the radiation 14 and which is combined with a sheet-like contact sensor (contact detecting unit) 32 for detecting when the patient 18 contacts the casing 28. The contact sensor 32 may comprise, for example, a piezoelectric sensor for converting a pressing force (pressure variation) applied to the contact sensor 32 into a contact detection signal when the patient 18 contacts the contact sensor 32 and presses the contact sensor 32 toward the irradiated surface 30.

The casing 28 houses therein a grid 34 for removing scattered rays of the radiation 14 from the patient 18, a temperature sensor (temperature detecting unit) 36, a radiation detector 40 for detecting the radiation 14 that has passed through the patient 18, and a lead plate 42 for absorbing back scattered rays of the radiation 14, which are successively arranged in the order named from the irradiated surface 30. The irradiated surface 30 of the casing 28 may be constructed as the grid 34.

Figure 4:
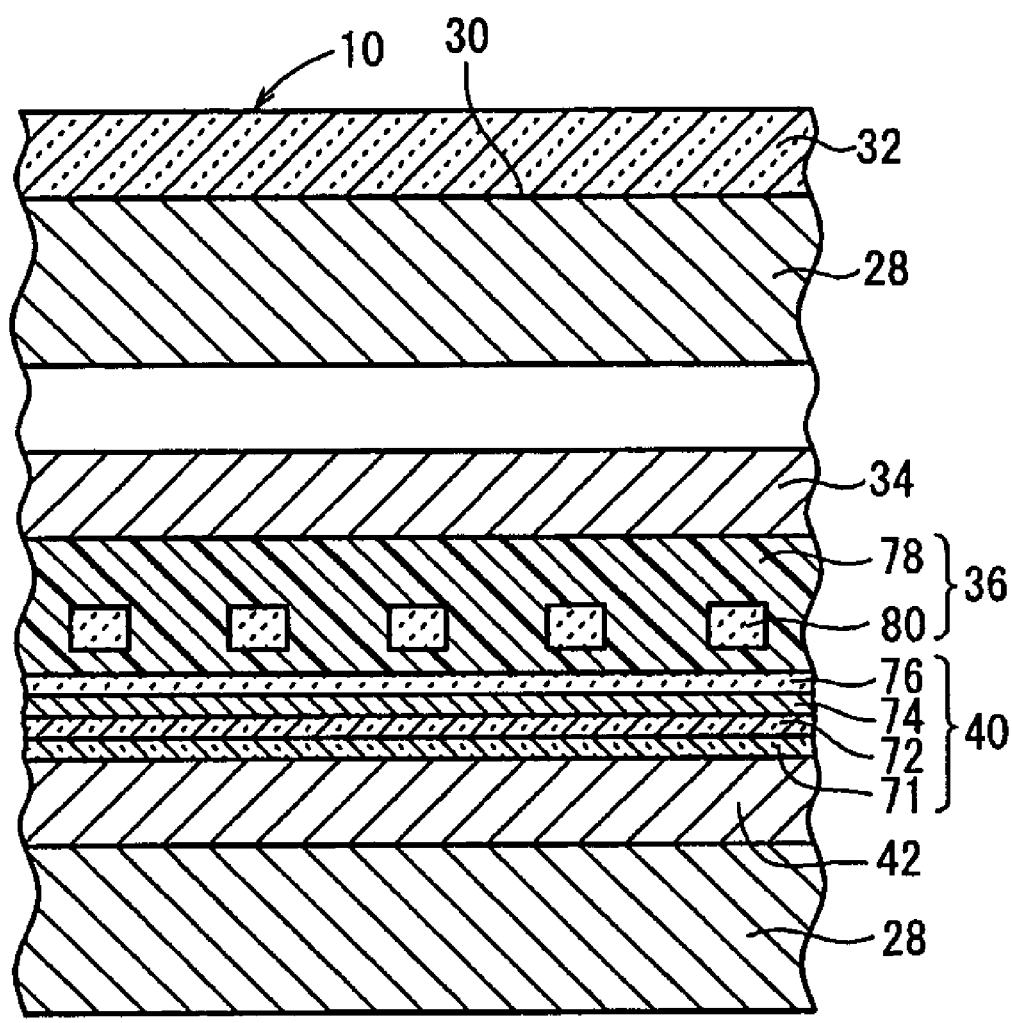
FIG. 4 is a cross-sectional view taken along line IV-IV of FIG. 2.

As shown in FIG. 4, the radiation detector 40 comprises a substrate 71, a scintillator 72 disposed on the substrate 71 and made of a phosphor such as GOS ($Gd_2O_2S$) or CsI for converting the radiation 14 which has passed through the patient 18 into visible light, a TFT layer 74 disposed on the scintillator 72 and including an array of thin-film transistors (TFTS) 52 (see FIG. 5), the TFT layer 74 being permeable to the radiation 14 and the visible light, and a photoelectric transducer layer 76 disposed on the TFT layer 74 and including solid-state detectors (hereinafter referred to as pixels) 50 made of a material such as amorphous silicon (a-Si) or the like, for converting the visible light into an electric signal.

The temperature sensor 36 comprises an electric insulating layer 78 and a plurality of temperature detectors 80 disposed in the electric insulating layer 78 at given spaced intervals and arrayed along the photoelectric transducer layer 76. Each of the temperature detectors 80, which may comprise a thermistor or the like, detects the temperature of the corresponding pixel 50 which faces the temperature detector 80 and outputs a temperature detection signal representative of the detected temperature. The temperature sensor 36 detects the temperatures of the respective pixels 50 as the surface temperature of (the photoelectric transducer layer 76 of) the radiation detector 40.

As shown in FIG. 2, the casing 28 also houses therein a battery 44 as a power supply of the radiation detecting cassette 10, a cassette controller 46 for energizing the radiation detector 40 with electric power supplied from the battery 44, and a transceiver (wireless communicating unit) 48 for sending and receiving signals including the information of the radiation 14 detected by the radiation detector 40, to and from the console 20. A shield plate of lead or the like should preferably be placed between the irradiated surface 30 of the casing 28 and the cassette controller 46 and the transceiver 48 to protect the cassette controller 46 and the transceiver 48 against damage which would otherwise be caused if irradiated with the radiation 14. The battery 44 supplies electric power to the contact sensor 32, the temperature sensor 36, the radiation detector 40, the cassette controller 46, and the transceiver 48 in the radiation detecting cassette 10.

Figure 5:
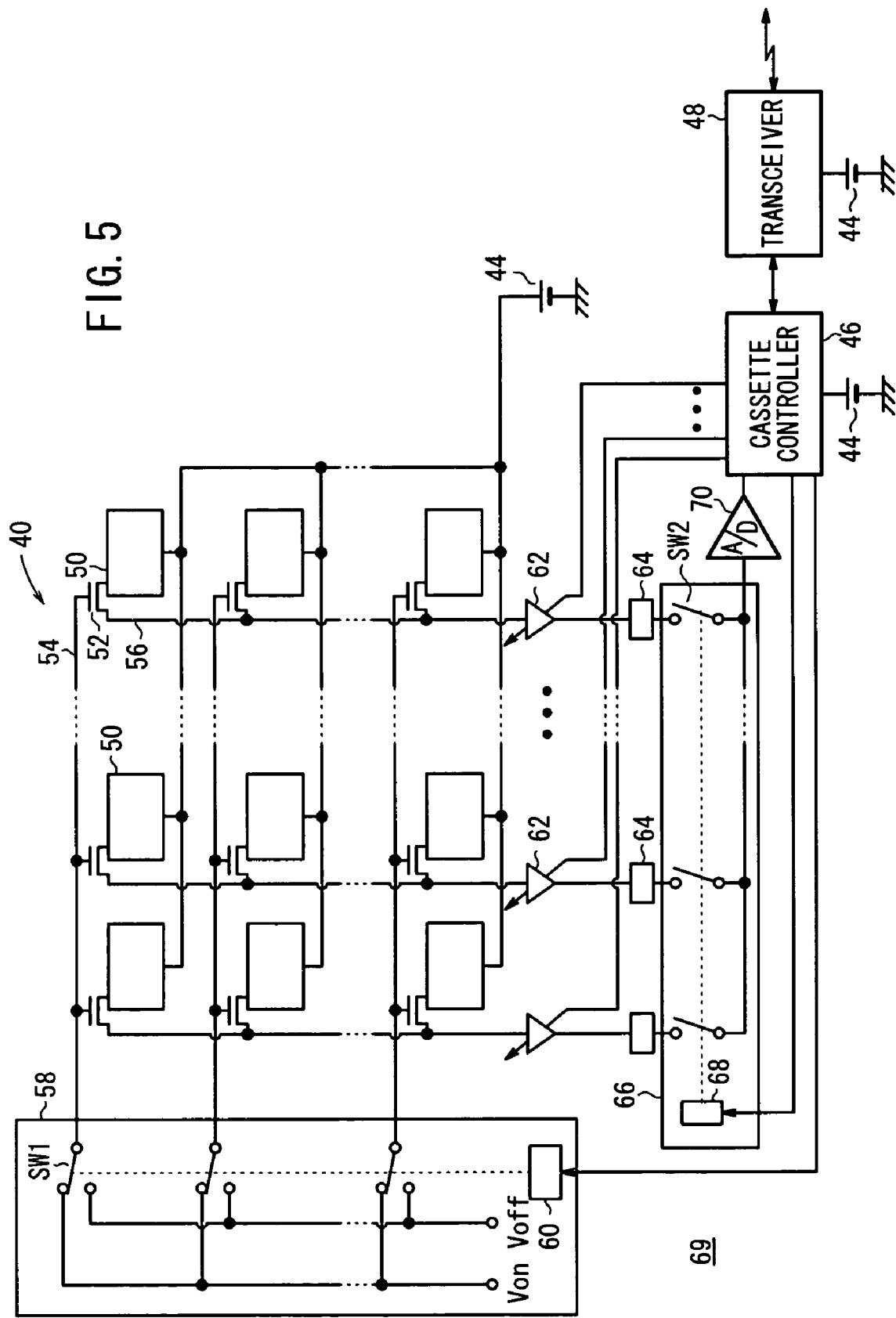
FIG. 5 is a block diagram of a circuit arrangement of a radiation detector in the radiation detecting cassette shown in FIG. 2.

FIG. 5 shows in block form a circuit arrangement of the radiation detector 40. As shown in FIG. 5, the radiation detector 40 comprises an array of thin-film transistors (TFTS) 52 arranged in rows and columns (the TFT layer 74), with the photoelectric transducer layer 76 disposed on the array of TFTs 52. The photoelectric transducer layer 76 is made of a material such as amorphous silicon or the like, for converting the visible light into an electric signal. When the radiation 14 is applied to the radiation detector 40, the photoelectric transducer layer 76 generates electric charges, and the pixels 50 store the generated electric charges. Then, the TFTs 52 are turned on along each row at a time to read the electric charges from the pixels 50 as an image signal.

The TFTs 52 connected to the respective pixels 50 are connected to respective gate lines 54 extending parallel to the rows and respective signal lines 56 extending parallel to the columns. The gate lines 54 are connected to a line scanning driver 58, and the signal lines 56 are connected to a multiplexer 66. The gate lines 54 are supplied with control signals Von, Voff for turning on and off the TFTs 52 along the rows from the line scanning driver 58. The line scanning driver 58 comprises a plurality of switches SW1 for switching between the gate lines 54 and an address decoder 60 for outputting a selection signal for selecting one of the switches SW1 at a time. The address decoder 60 is supplied with an address signal from the cassette controller 46.

The signal lines 56 are supplied with electric charges stored in the pixels 50 through the TFTs 52 arranged in the columns. The electric charges supplied to the signal lines 56 are amplified by amplifiers 62 connected respectively to the signal lines 56. The amplifiers 62 are connected through respective sample and hold circuits 64 to the multiplexer 66. The multiplexer 66 comprises a plurality of switches SW2 for successively switching between the signal lines 56 and an address decoder 68 for outputting a selection signal for selecting one of the switches SW2 at a time. The address decoder 68 is supplied with an address signal from the cassette controller 46. The multiplexer 66 has an output terminal connected to an A/D converter 70. A radiation image signal generated by the multiplexer 66 based on the electric charges from the sample and hold circuits 64 is converted by the A/D converter 70 into a digital image signal representing radiation image information, which is supplied to the cassette controller 46.

The components of the radiation detector 40 which range from the line scanning driver 58 to the TFTs 52 and from the TFTs 52 to the A/D converter 70 serve as a reading circuit (reader) 69 for reading electric charges (electric signal) from the pixels 50 and acquiring the read electric charges as radiation image information.

The TFTs 52 which function as switching devices may be combined with another image capturing device such as a CMOS (Complementary Metal-Oxide Semiconductor) image sensor or the like. Alternatively, the TFTs 52 may be replaced with a CCD (Charge-Coupled Device) image sensor for shifting and transferring electric charges with shift pulses which correspond to gate signals in the TFTs.

As shown in FIG. 1, the cassette controller 46 of the radiation detecting cassette 10 includes an address signal generator 82, an image memory 84, a cassette ID memory 86, and a sensitivity corrector (corrector) 88.

The address signal generator 82 supplies address signals to the address decoder 60 of the line scanning driver 58 and the address decoder 68 of the multiplexer 66 of the radiation detector 40. The image memory 84 stores the radiation image information detected by the radiation detector 40. The cassette ID memory 86 stores cassette ID information for identifying the radiation detecting cassette 10.

The sensitivity corrector 88 judges that the patient 18 is held in contact with the casing 28 with the contact sensor 32 interposed therebetween when it is supplied with a contact detection signal from the contact sensor 32. The sensitivity corrector 88 also performs a temperature compensation process for correcting the sensitivity of the radiation detector 40 based on the temperatures of the pixels 50, i.e., the surface temperature of the photoelectric transducer layer 76 of the radiation detector 40, which are represented by the temperature detection signals from the temperature detectors 80.

While the patient 18 is being irradiated with the radiation 14, i.e., while the radiation image information of the patient 18 is being captured, the heat based on the temperature of the patient 18 is transferred to the radiation detector 40 housed in the casing 28 because the patient 18 is held in contact with the radiation detecting cassette 10. Therefore, the temperature of (the pixels 50) the photoelectric transducer layer 76 of the radiation detector 40 is increased, tending to change the sensitivity of the radiation detector 40, i.e., the sensitivity of the electric charges output from the pixels 50. Within the period of time in which the sensitivity corrector 88 is supplied with the contact detection signal, the sensitivity corrector 88 adjusts the gains of the amplifiers 62 which amplify the electric charges flowing through the TFTs 52 from those pixels 50 which face the temperature detectors 80 that have detected temperatures higher than a predetermined threshold temperature, for thereby temperature compensation for a change in the sensitivity of the radiation detector 40.

The transceiver 48 transmits the cassette ID information stored in the cassette ID memory 86 and the radiation image information stored in the image memory 84 to the console 20 by way of wireless communications.

Figure 6:
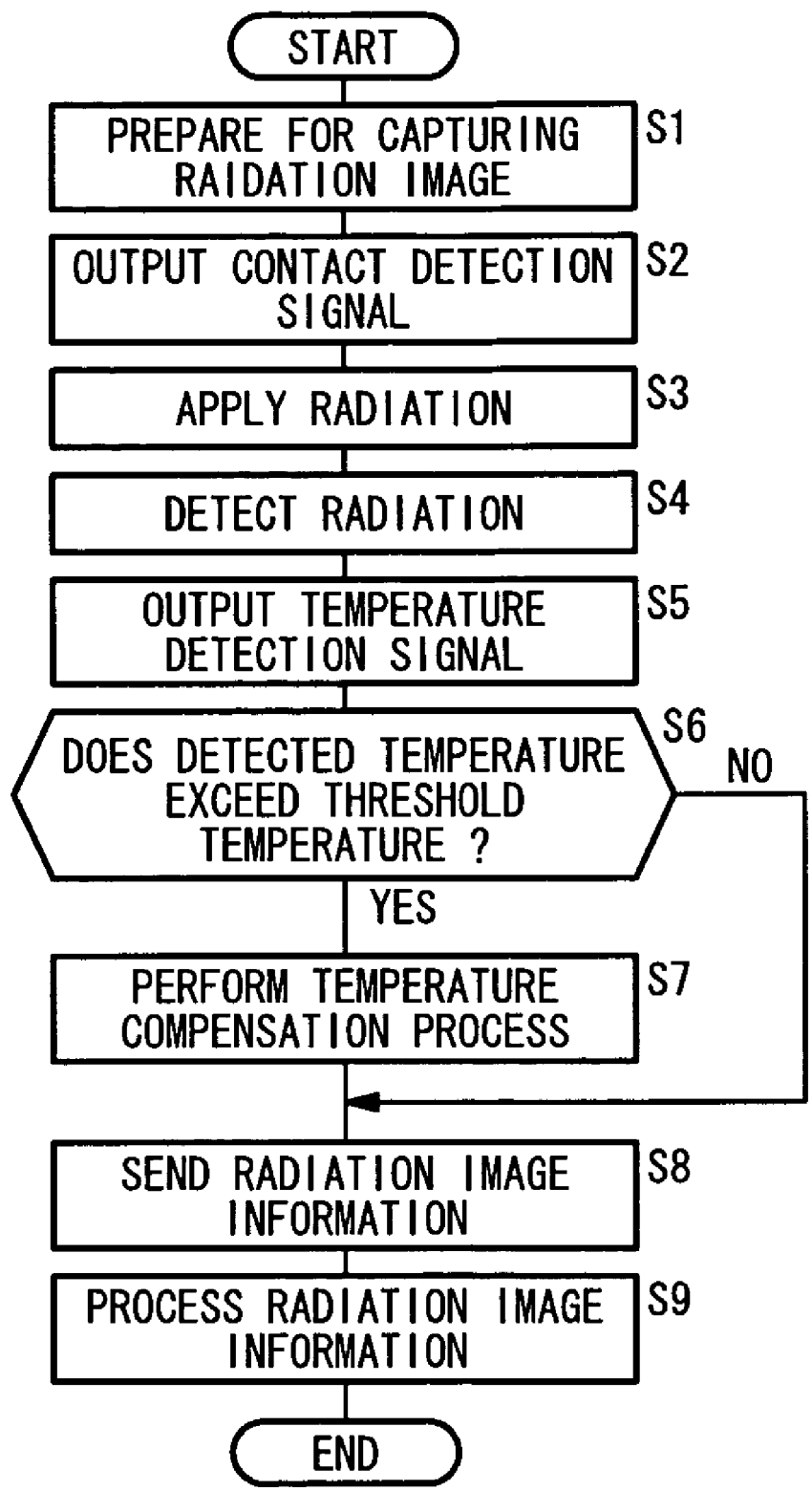
FIG. 6 is a flowchart of an operation sequence of the radiation image capturing system shown in FIG. 1.

The radiation detecting cassette 10 and the radiation image capturing system 12 according to the present embodiment are basically constructed as described above. Operation, including a temperature compensation method, of the radiation detecting cassette 10 and the radiation image capturing system 12 will be described below with reference to a flowchart shown in FIG. 6.

In step S1, patient information of the patient 18 to be imaged is registered in the console 20 in advance of an image capturing process. If a region to be imaged and an image capturing method are already known, then these image capturing conditions are also registered in the console 20.

For capturing radiation image information of the patient 18 when the doctor performs a surgical operation on the patient 18 is in the operating room, or when the doctor examines the patient 18, or when the doctor goes the rounds in the hospital, the doctor or the radiological technician places the radiation detecting cassette 10 between the patient 18 and the bed with the irradiated surface 30 facing the radiation source 16. At this time, since the patient 18 contacts the irradiated surface 30 with the contact sensor 32 interposed therebetween, the contact sensor 32 outputs a contact detection signal to the sensitivity corrector 88 in step S2.

Then, after having moved the radiation source 16 to a position facing the radiation detecting cassette 10, the doctor or the radiological technician operates an image capturing switch of the radiation source 16 to start the image capturing process.

When the image capturing switch is operated, the radiation source 16 sends a request to the console 20 to transmit the image capturing conditions by way of wireless communications. In response to the request, the console 20 transmits the image capturing conditions with respect to the region to be imaged of the patient 18 to the radiation source 16. When the radiation source 16 receives the image capturing conditions, the radiation source 16 applies a radiation 14 at a dosage according to the image capturing conditions to the patient 18 in step S3.

The radiation 14 which has passed through the patient 18 is applied to the grid 34 of the radiation detecting cassette 10, which removes scattered rays from the radiation 14. Then, the radiation 14 is applied to the radiation detector 40. The scintillator 72 of the radiation detector 40 emits visible light at an intensity depending on the intensity of the applied radiation 14. The pixels 50 of the photoelectric transducer layer 76 convert the visible light into electric signals and store them as electric charges in step S4. The stored electric charges, which represent radiation image information of the patient 18, are read from the pixels 50 according to address signals which are supplied from the address signal generator 82 of the cassette controller 46 to the line scanning driver 58 and the multiplexer 66.

Specifically, in response to the address signal supplied from the address signal generator 82, the address decoder 60 of the line scanning driver 58 outputs a selection signal to select one of the switches SW1, which supplies the control signal Von to the gates of the TFTs 52 connected to the gate line 54 corresponding to the selected switch SW1. In response to the address signal supplied from the address signal generator 82, the address decoder 68 of the multiplexer 66 outputs a selection signal to successively turn on the switches SW2 to switch between the signal lines 56 for thereby reading the electric charges stored in the pixels 50 connected to the selected gate line 54, through the signal lines 56.

The electric charges read from the pixels 50 connected to the selected gate line 54 of the radiation detector 40 are amplified by the respective amplifiers 62, sampled by the sample and hold circuits 64, and supplied to the multiplexer 66. Based on the supplied electric charges, the multiplexer 66 generates and supplies a radiation image signal to the A/D converter 70, which converts the radiation image signal into a digital signal. The digital signal which represents the radiation image information is stored in the image memory 84 of the cassette controller 46.

Similarly, the address decoder 60 of the line scanning driver 58 successively turns on the switches SW1 to switch between the gate lines 54 according to the address signal supplied from the address signal generator 82. The electric charges stored in the pixels 50 connected to the successively selected gate lines 54 are read through the signal lines 56, and processed by the multiplexer 66 and the A/D converter 70 into digital signals, which are stored in the image memory 84 of the cassette controller 46.

At this time, the temperature detectors 80 of the temperature sensor 36 detect the temperatures of the respective pixels 50 which confront the temperature detectors 80, i.e., the surface temperature of the photoelectric transducer layer 76 of the radiation detector 40, and output the temperature detection signals representative of the detected temperatures to the sensitivity corrector 88 in step S5. While the sensitivity corrector 88 is being supplied with the contact detection signal, it determines whether the temperature indicated by the temperature detection signal exceeds the threshold temperature or not in step S6. If there are any temperature detectors 80 which have detected temperatures in excess of the threshold temperature (YES in step S6), then the sensitivity corrector 88 judges that the sensitivity of the electric charges (electric signal) output from the pixels 50 which face the temperature detectors 80 has changed due to the heat transferred from the patient 18 through the casing 28 to the radiation detector 40, and performs the temperature compensation method for adjusting the gain of the amplifiers 62 which are supplied with the electric charges from those pixels 50 in step S7.

If there are no temperature detectors 80 which have detected temperatures in excess of the threshold temperature (NO in step S6), then sensitivity corrector 88 does not perform the temperature compensation method in step S7.

The radiation image information stored in the image memory 84 is transmitted from the transceiver 48 to the console 20 by way of wireless communications in step S8. In step S9, the console 20 performs a predetermined image processing process on the received radiation image information, and stores the processed radiation image information in a memory in association with the registered patient information of the patient 18. The processed radiation image information is transmitted from the console 20 to the display device 22, which displays a radiation image based on the radiation image information.

With the radiation detecting cassette 10 and the radiation image capturing system 12 according to the present embodiment, since the sensitivity corrector 88 corrects the sensitivity of the radiation detector 40 based on the temperatures of the pixels 50, i.e., the surface temperature of the photoelectric transducer layer 76 of the radiation detector 40, detected by the temperature detectors 80 of the temperature sensor 36, the radiation detector 40 can reliably be temperature-compensated for a change in its sensitivity due to a change in the temperature of the radiation detector 40.

Inasmuch as the radiation detecting cassette 10 which is portable has the above temperature compensating function, the radiation detecting cassette 10 can easily be reduced in weight and thickness. Specifically, the built-in radiation detecting cassette disclosed in Japanese Laid-Open Patent Publication No. 2006-128890 can be controlled in temperature by an air-cooling fan or a water-cooling mechanism. If a portable radiation detecting cassette like the radiation detecting cassette 10 is combined with an air-cooling fan or a water-cooling mechanism, then it is difficult to reduce the weight and thickness of the portable radiation detecting cassette. Since the radiation detecting cassette 10 with the above temperature compensating function is free of an air-cooling fan or a water-cooling mechanism, it can easily be reduced in weight and thickness and can be constructed in the form of a flexible sheet assembly.

The sensitivity corrector 88 corrects the sensitivities of the electric charges (electric signal) read from the respective pixels 50 based on the temperatures of the pixels 50. Therefore, the sensitivity corrector 88 can effectively reduce changes in the sensitivities of the electric charges due to a change in the temperature of the radiation detector 40.

Furthermore, the sensitivity corrector 88 corrects the sensitivities of the electric charges after the contact sensor 32 detects that the patient 18 contacts the casing 28. Consequently, the sensitivity corrector 88 can efficiently reduce changes in the sensitivities of the electric charges due to an increase in the temperatures of the pixels 50 which is caused by the heat transferred from the patient 18 through the casing 28 to the radiation detector 40. As the sensitivity corrector 88 performs the temperature compensation process on the radiation detector 40 while it is being supplied with the contact detection signal from the contact sensor 32, the sensitivity corrector 88 is reliably prevented from performing the temperature compensation process when the patient 18 is not held in contact with the casing 28, i.e., when no radiation image information is not captured.

As the scintillator 72, the TFT layer 74, and the photoelectric transducer layer 76 are successively disposed on the substrate 71, or stated otherwise, the photoelectric transducer layer 76, the TFT layer 74, and the scintillator 72 are successively disposed on the irradiated surface 30, the visible light generated by the scintillator 72 can efficiently be converted into an electric signal by the photoelectric transducer layer 76. As a result, the radiation detector 40 can produce radiation image information of high image quality.

In the above embodiment, the temperature detectors 80 detect the temperatures of the pixels 50, and the sensitivity corrector 88 corrects the sensitivity of the radiation detector 40 based on the detected temperatures of the pixels 50. However, the body temperature of the patient 18 on its surface contacting the contact sensor 32 may be detected, the sensitivity corrector 88 may estimate the temperatures of the pixels 50 from the detected body temperature of the patient 18, and may correct the sensitivity of the radiation detector 40 based on the estimated temperatures of the pixels 50. According to such a modification, the contact sensor 32 incorporates an array of temperature detectors 80 (body temperature detecting unit) therein, and the sensitivity corrector 88 identifies a region to be imaged of the patient 18 based on the area of contact of the patient 18 with the contact sensor 32 and the positions of those temperature detectors 80 which have detected by the body temperature of the patient 18. If the estimated temperatures of the pixels 50 which face the identified region to be imaged of the patient 18 are in excess of the threshold temperature, then the sensitivity corrector 88 corrects the sensitivities of the electric charges output from those pixels 50.

Furthermore, rather than correcting the sensitivity of the radiation detector 40 with the sensitivity corrector 88 based on the temperatures of the pixels 50, temperature compensation processes (1) through (3) to be described below may be performed: (1) If a dark current (electric charge offset) is generated by electric charges which are accumulated in the pixels 50 even though no visible light is applied to the photoelectric transducer layer 76, then a corrector corrects the dark current based on the temperatures of the pixels 50. (2) If density steps are produced between the amplifiers 62 as integral amplifiers, i.e., if level differences are developed between the electric charges amplified by the amplifiers 62, then a corrector corrects the density steps based on the temperatures of the pixels 50. (3) If a residual image of the radiation image information produced by a preceding imaging cycle is accumulated as electric charges in the pixels 50, then a corrector corrects the levels of electric charges output from the pixels 50 in a present imaging cycle based on the temperatures of the pixels 50. According to the above temperature compensation processes (1) through (3), temperature compensation can reliably be carried out with respect to a change in at least one of the dark current, the density steps, and the residual image of the radiation detector 40 which is caused by a change in the temperatures of the pixels 50.

Accordingly, it is possible to reliably carry out temperature compensation with respect to a change in at least one of the sensitivity, the dark current, the density steps, and the residual image of the radiation detector 40 which is caused by a change in the temperatures of the pixels 50.

According to the present embodiment, furthermore, since signals are sent and received by way of wireless communications between the console 20, the radiation detecting cassette 10, the radiation source 16, and the display device 22, no cables for transmitting and receiving signals are required therebetween, and hence there are no cable-induced obstacles to the operation performed by the doctor and the radiological technician. Therefore, the doctor and the radiological technician are allowed to perform their work smoothly and efficiently.

According to the present embodiment, moreover, radiation image information is captured when the doctor or the radiological technician turns on the image capturing switch. However, radiation image information may be captured when the doctor or the radiological technician operates the console 20.

Figure 7:
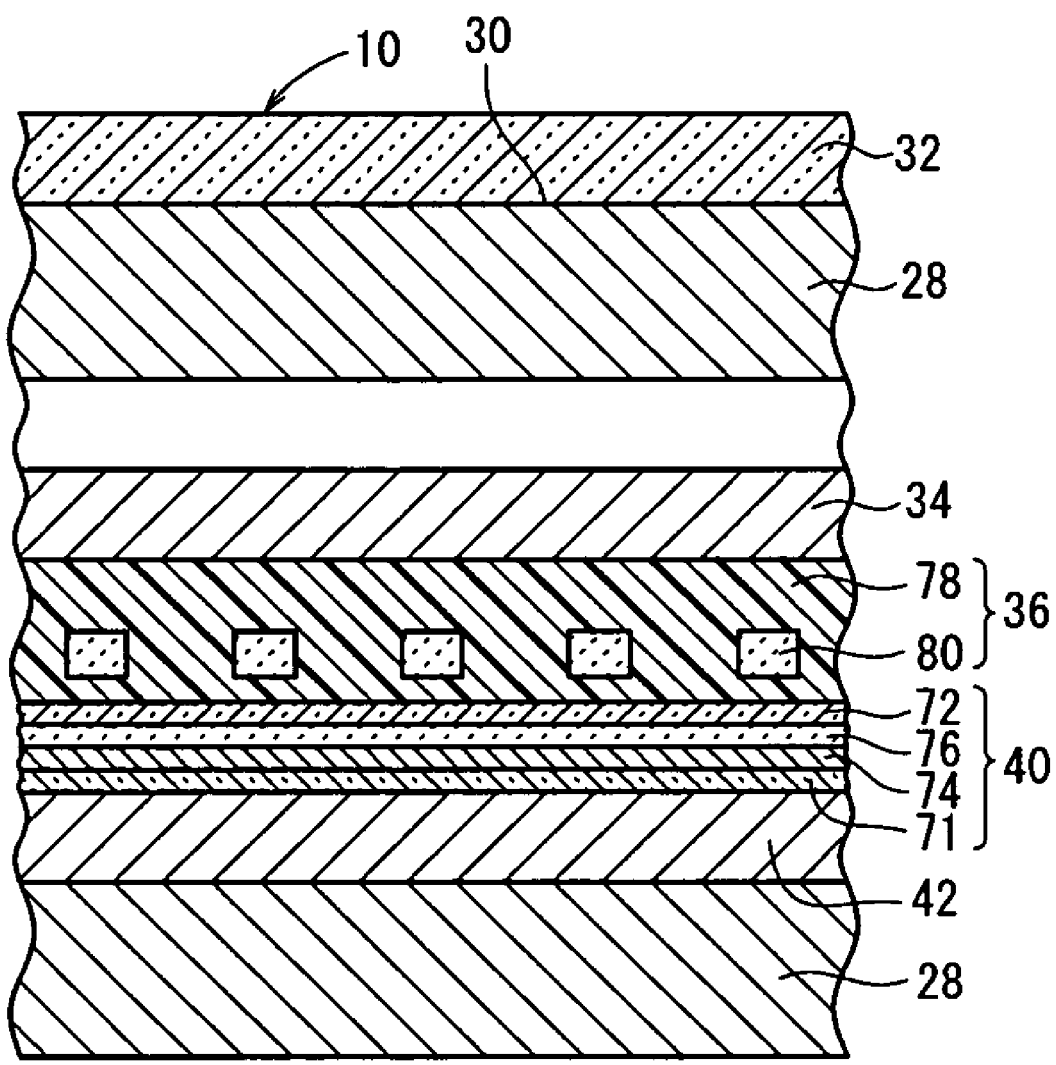
FIG. 7 is a cross-sectional view of a modified radiation detecting cassette, similar to a cross-sectional view taken along line VII-VII of FIG. 2.

FIG. 7 shows in cross section a modified radiation detecting cassette 10. As shown in FIG. 7, the modified radiation detecting cassette 10 includes the TFT layer 74, the photoelectric transducer layer 76, and the scintillator 72 which are successively arranged in the order named from the substrate 71 toward the irradiated surface 30. With the modified radiation detecting cassette 10, visible light converted by the scintillator 72 can be converted into an electric signal by the photoelectric transducer layer 76, and the temperatures of the pixels 50 of the photoelectric transducer layer 76 can reliably be detected by the temperature detectors 80. The modified radiation detecting cassette 10 can thus offer the same advantages as those described above.

The dosage of the applied radiation 14 may be converted directly into an electric signal by a photoelectric transducer layer which comprises solid-state detectors made of a material such as amorphous selenium (a-Se).

The radiation image capturing system 12 may employ a light-reading radiation detector for acquiring radiation image information. The light-reading radiation detector operates as follows: When a radiation is applied to a matrix of solid-state detecting devices, the solid-state detecting devices store an electrostatic latent image depending on the dosage of the applied radiation. For reading the stored electrostatic latent image, reading light is applied to the radiation detector to cause the radiation detector to generate electric current representing radiation image information. When erasing light is applied to the radiation detector, radiation image information representing a residual electrostatic latent image is erased from the radiation detector, which can thus be reused (see Japanese Laid-Open Patent Publication No. 2000-105297).

When the radiation detecting cassette 10 is used in the operating room or the like, blood stains and contaminants may be applied to the radiation detecting cassette 10. The radiation detecting cassette 10 may be of a water-resistant, sealed structure so that it can be sterilized and cleaned to remove such blood stains and contaminants for repetitive use.

The radiation detecting cassette 10 and an external device may communicate with each other by way of optical wireless communications using infrared rays or the like, rather than usual wireless communications using radio waves.

Figure 8:
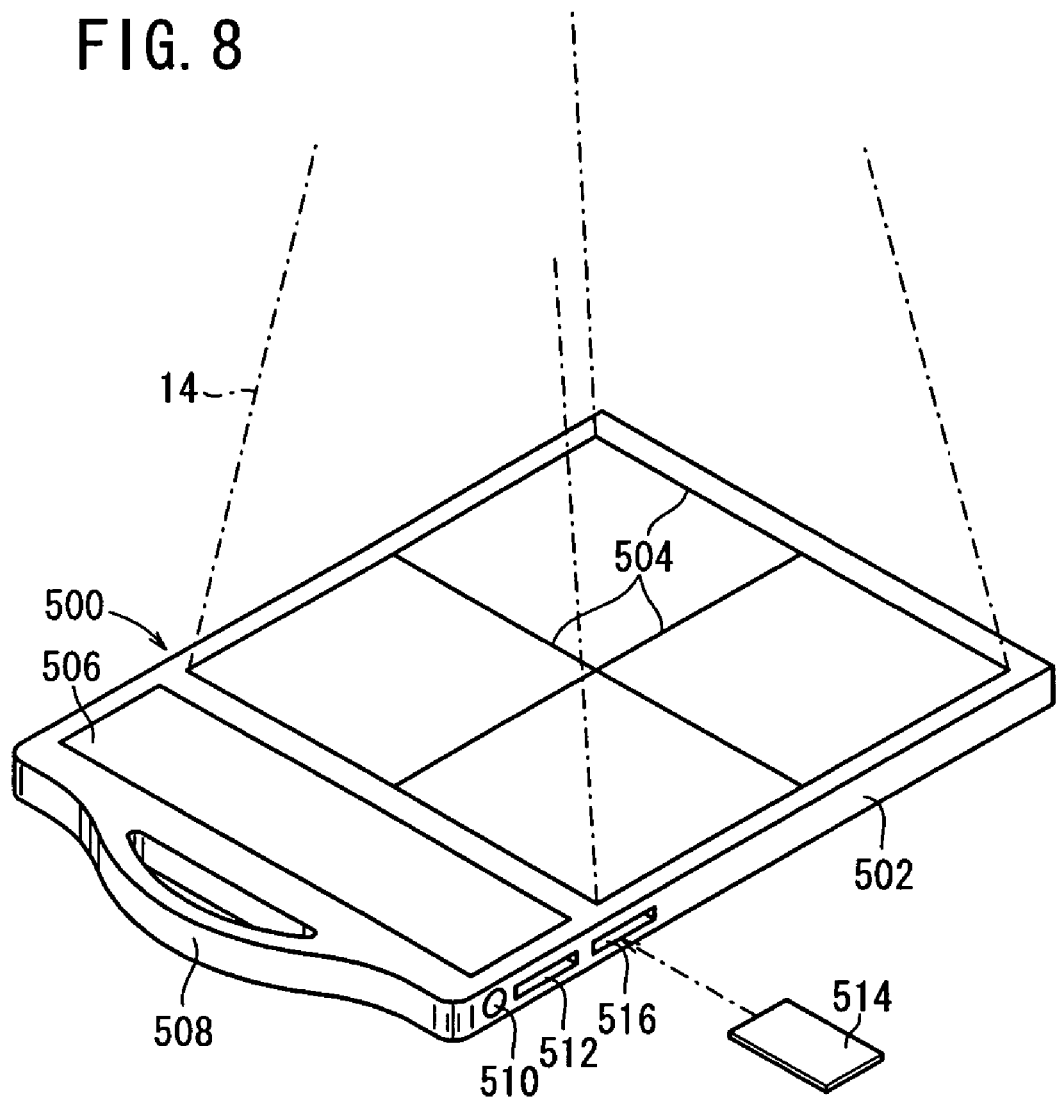
FIG. 8 is a perspective view of a radiation detecting cassette according to another embodiment of the present invention.

FIG. 8 shows in perspective a radiation detecting cassette 500 according to another embodiment of the present invention.

As shown in FIG. 8, the radiation cassette 500 has guide lines 504 drawn on the irradiated surface of a casing 502 as a reference mark for an image capturing area and an image capturing position. Using the guide lines 504, the subject to be imaged, such as the patient 18, can be positioned with respect to the radiation detecting cassette 500 and the range in which the radiation is to be applied to the radiation detecting cassette 500 can be determined, for thereby recording radiation image information in an appropriate image capturing area of the radiation detecting cassette 500.

The radiation detecting cassette 500 also has a display unit 506 outside of the image capturing area thereof for displaying various items of information about the radiation detecting cassette 500. Specifically, the display unit 506 displays ID information of the patient 18 whose radiation image information is recorded in the radiation detecting cassette 500, the number of times that the radiation detecting cassette 500 has been used, an accumulated exposed dosage, the charged state (remaining power level) of the battery 44 housed in the radiation detecting cassette 500, image capturing conditions for radiation image information, and a positioning image representing the patient 18 positioned with respect to the radiation detecting cassette 500, etc. The radiological technician can confirm the patient 18 based on the ID information displayed on the display unit 506, also confirm in advance that the radiation detecting cassette 500 is in a usable state, position the desired area to be imaged of the patient 18 with respect to the radiation detecting cassette 500 based on the displayed positioning image, and capture optimum radiation image information in the radiation detecting cassette 500.

The radiation detecting cassette 500 includes a handle 508 to be gripped by the user to handle and carry the radiation detecting cassette 500 with ease.

The radiation detecting cassette 500 also has an input terminal 510 for connection to an AC adapter, a USB (Universal Serial Bus) terminal 512, and a card slot 516 for receiving a memory card 514, all provided on a side wall of the casing of the radiation detecting cassette 500.

When the charging function of the battery 44 housed in the radiation detecting cassette 500 is low or when there is not enough time to charge the battery 44, an AC adapter is connected to the input terminal 510 to supply electric power from an external source for thereby making the radiation detecting cassette 500 immediately usable.

The USB terminal 512 or the card slot 516 can be used when the radiation detecting cassette 500 is unable to send and receive information to and from an external device such as the console 20 or the like by way of wireless communications. Specifically, by connecting a cable to the USB terminal 512, the radiation detecting cassette 500 can send and receive information to and from the external device by way of wired communications.

Alternatively, the memory card 514 is inserted into the card slot 516 and necessary information from the radiation detecting cassette 500 is recorded into the memory card 514. Thereafter, the memory card 514 is disconnected and connected to the external device to send the information to the external device.

Figure 9:
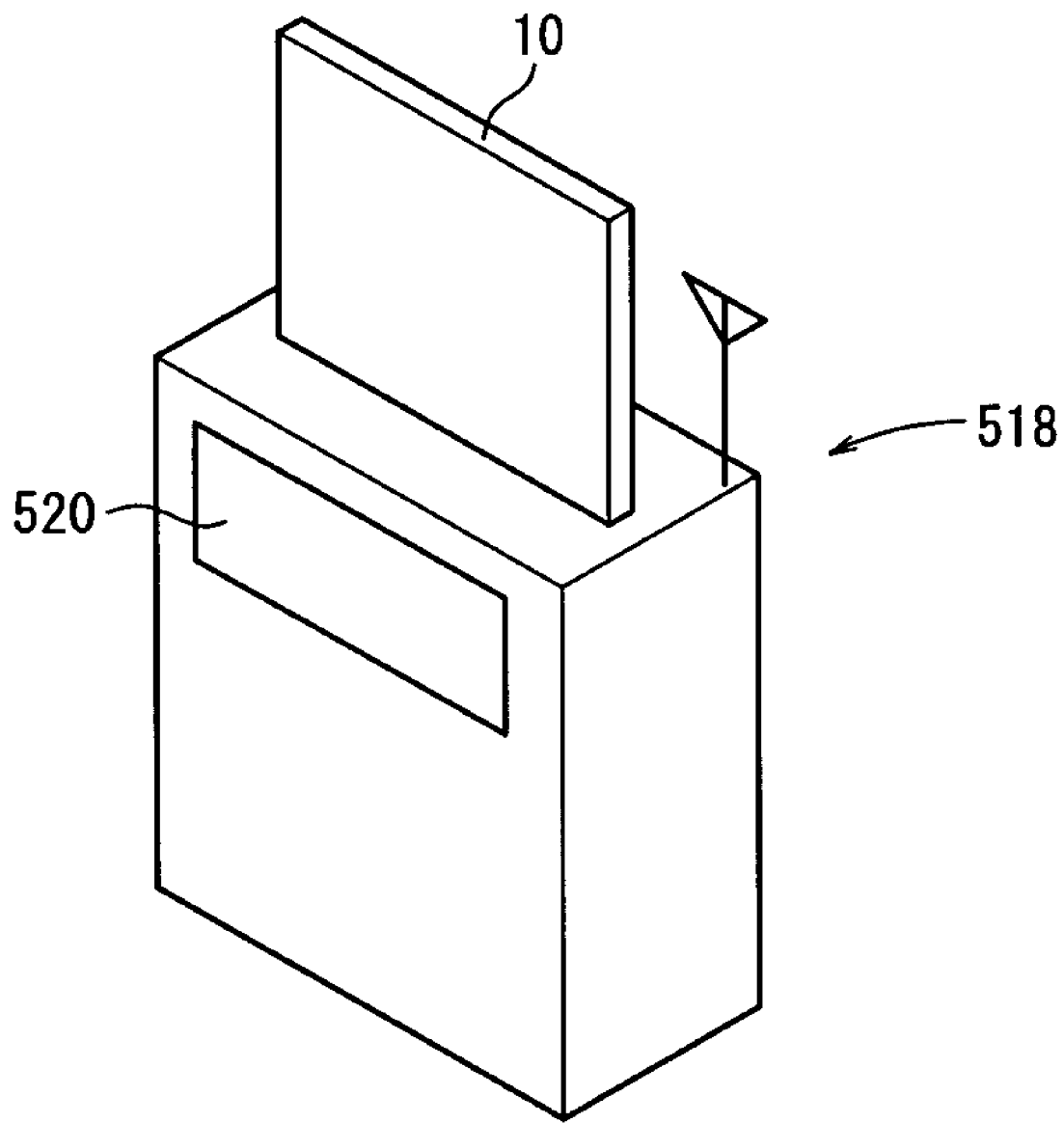
FIG. 9 is a perspective view of a cradle for charging a battery in the radiation detecting cassette.

FIG. 9 shows a cradle 518 for receiving the radiation detecting cassette 10 and charging the battery 44 housed in the radiation detecting cassette 10. The cradle 518 is positioned in the operating room or a desired location in the hospital. The cradle 518 may not only be able to charge the battery 44, but also have a wireless or wired communication function to send and receive necessary information to and from an external device, such as the RIS 24, the HIS 26, the console 20, or the like. The information that is sent from the cradle 518 may include radiation image information recorded in the radiation detecting cassette 10 loaded in the cradle 518.

The cradle 518 has a display unit 520 for displaying the charged state of the battery 44 housed in the radiation detecting cassette 10 which is loaded in the cradle 518 and necessary information including radiation image information acquired from the radiation detecting cassette 10 which is loaded in the cradle 518.

A plurality of cradles 518 may be connected to a network, and charged states of the batteries 44 housed in the radiation detecting cassettes 10 loaded in the respective cradles 518 may be retrieved through the network, so that the user can confirm the locations of any radiation detecting cassettes 10 whose batteries 44 are sufficiently charged, based on the retrieved charged states of the batteries 44.

Although certain preferred embodiments of the present invention have been shown and described in detail, it should be understood that various changes and modifications may be made therein without departing from the scope of the appended claims.

What is claimed is:

1. A radiation detecting apparatus comprising:
    a radiation conversion panel for detecting a radiation which has passed through a subject and converting the detected radiation into radiation image information;
    a temperature detecting unit for detecting a temperature of the radiation conversion panel; and
    a corrector for correcting at least one of a sensitivity, a dark current, a density step, and a residual image of the radiation conversion panel based on the temperature detected by the temperature detecting unit,
    wherein the radiation conversion panel comprises a scintillator for converting the radiation into visible light and a plurality of solid-state detectors for converting the visible light into electric signals, and
    wherein the solid-state detectors and the scintillator are successively arranged in the order named along an irradiation direction.

2. A radiation detecting apparatus according to claim 1, wherein the radiation detecting apparatus comprises a portable radiation detecting apparatus; and
    the temperature detecting unit detects a surface temperature of the radiation conversion panel.

3. A radiation detecting apparatus according to claim 2, wherein the radiation conversion panel comprises a reader for reading the electric signals from the solid-state detectors and acquiring the read electric signals as the radiation image information;
    the temperature detecting unit detects temperatures of the solid-state detectors as the surface temperature of the radiation conversion panel; and
    the corrector corrects at least one of the sensitivity, the dark current, the density step, and the residual image, of the electrical signals read by the reader, based on the surface temperature of the radiation conversion panel.

4. A radiation detecting apparatus according to claim 3, further comprising:
    a substantially rectangular casing, the radiation conversion panel, the temperature detecting unit, and the corrector being housed in the substantially rectangular casing, the substantially rectangular casing having an irradiated surface which is irradiated with the radiation; and
    a contact detecting unit disposed on the irradiated surface, for detecting when the subject is brought into contact with the substantially rectangular casing;
    wherein the corrector corrects at least one of the sensitivity, the dark current, the density step, and the residual image, of the electric signals, based on the surface temperature of the radiation conversion panel after the contact detecting unit detects that the subject is brought into contact with the substantially rectangular casing.

5. A radiation detecting apparatus according to claim 4, wherein the radiation detecting apparatus comprises a radiation detecting cassette; and
    the substantially rectangular casing is made of a material permeable to the radiation.

6. A radiation detecting apparatus according to claim 1, wherein the temperature detecting unit detects a temperature of the subject which is held in contact with the radiation detecting apparatus, and estimates the temperature of the radiation conversion panel based on the detected temperature of the subject; and
    the corrector corrects at least one of the sensitivity, the dark current, the density step, and the residual image of the radiation conversion panel based on the estimated temperature of the radiation conversion panel.

7. A radiation detecting apparatus according to claim 1, further comprising:
    a wireless communicating unit for performing wireless communications with an external device; and
    a battery for energizing the radiation conversion panel, the temperature detecting unit, the corrector, and the wireless communicating unit.

8. A radiation image capturing system comprising:
    a radiation source for applying a radiation to a subject;
    a radiation detecting apparatus comprising a radiation conversion panel for detecting the radiation which has passed through the subject and converting the detected radiation into radiation image information, a temperature detecting unit for detecting a temperature of the radiation conversion panel, and a corrector for correcting at least one of a sensitivity, a dark current, a density step, and a residual image of the radiation conversion panel based on the temperature detected by the temperature detecting unit; and
    a control apparatus for controlling the radiation source and the radiation detecting apparatus, wherein the radiation conversion panel comprises a scintillator for converting the radiation into visible light and a plurality of solid-state detectors for converting the visible light into electric signals, and wherein the solid-state detectors and the scintillator are successively arranged in the order named along an irradiation direction.

9. A radiation image capturing system according to claim 8, wherein the radiation detecting apparatus sends the radiation image information converted by the radiation conversion panel to the control apparatus by way of wireless communications.

10. A temperature compensating method in detecting a radiation which has passed through a subject and converting the radiation into radiation image information with a radiation conversion panel, comprising the steps of:

detecting a temperature of the radiation conversion panel with a temperature detecting unit; and correcting at least one of a sensitivity, a dark current, a density step, and a residual image of the radiation conversion panel with a corrector based on the temperature detected by the temperature detecting unit, wherein the radiation conversion panel comprises a scintillator for converting the radiation into visible light and a plurality of solid-state detectors for converting the visible light into electric signals, and wherein the solid-state detectors and the scintillator are successively arranged in the order named along an irradiation direction.

* * * * *